(12) United States Patent
Cook et al.

(10) Patent No.: US 11,291,470 B2
(45) Date of Patent: Apr. 5, 2022

(54) SURGICAL PROBE WITH SHAPE-MEMORY MATERIAL

(71) Applicant: Novartis AG, Basel (CH)

(72) Inventors: Christopher Cook, Laguna Niguel, CA (US); Alireza Mirsepassi, Irvine, CA (US); Kambiz Parto, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 78 days.

(21) Appl. No.: 16/217,322

(22) Filed: Dec. 12, 2018

(65) Prior Publication Data

US 2019/0175217 A1    Jun. 13, 2019

Related U.S. Application Data

(60) Provisional application No. 62/597,550, filed on Dec. 12, 2017.

(51) Int. Cl.
| | | |
|---|---|---|
| *A61F 9/00* | (2006.01) | |
| *A61B 17/34* | (2006.01) | |
| *A61F 9/008* | (2006.01) | |
| *A61B 90/00* | (2016.01) | |
| *A61B 18/24* | (2006.01) | |
| *A61B 18/20* | (2006.01) | |

(Continued)

(52) U.S. Cl.
CPC .......... *A61B 17/3421* (2013.01); *A61B 18/20* (2013.01); *A61B 18/24* (2013.01); *A61B 90/36* (2016.02); *A61F 9/008* (2013.01); *A61F 9/00821* (2013.01); *G02B 6/3624* (2013.01); *A61B 17/00234* (2013.01); *A61B 18/082* (2013.01); *A61B 2017/00867* (2013.01); *A61B 2090/3614* (2016.02); *G02B 6/02042* (2013.01); *G02B 6/32* (2013.01)

(58) Field of Classification Search
CPC ..................................................... A61B 90/36
See application file for complete search history.

(56) References Cited

U.S. PATENT DOCUMENTS

| | | |
|---|---|---|
| 5,199,431 A | 4/1993 | Kittrell |
| 5,496,305 A | 3/1996 | Kittrell |

(Continued)

FOREIGN PATENT DOCUMENTS

| | | |
|---|---|---|
| JP | A1994014936 A | 1/1994 |
| JP | 2013048864 A | 3/2013 |

(Continued)

*Primary Examiner* — Gary Jackson
*Assistant Examiner* — Anant A Gupta (57) ABSTRACT

Various embodiments are generally directed to a surgical probe with shape-memory material, such as a probe with a set of light sources, for instance. Some embodiments are particularly directed to a cannula with a shape-memory material that is used to secure a window. In one or more embodiments, for example, an apparatus for surgical use may include a cannula with a shape-memory material in an austenitic phase. In some embodiments, the window may be positioned at an opening of the cannula when the shape-memory material is in a martensitic phase. In some embodiments, transitioning the shape-memory material from the martensitic phase to the austenitic phase secures the window in position at the opening of the cannula.

10 Claims, 5 Drawing Sheets

(51) Int. Cl.
*G02B 6/36* (2006.01)
*A61B 18/08* (2006.01)
*A61B 17/00* (2006.01)
*G02B 6/32* (2006.01)
*G02B 6/02* (2006.01)

(56) References Cited

U.S. PATENT DOCUMENTS

| | | |
|---|---|---|
| 5,625,638 A | 4/1997 | Trost |
| 5,693,043 A | 12/1997 | Kittrell |
| 5,921,981 A | 7/1999 | Bahmanyar et al. |
| 6,066,128 A | 5/2000 | Bahmanyar et al. |
| 6,092,898 A * | 7/2000 | de Juan, Jr. ............ A61B 3/125 351/159.02 |
| 6,096,028 A | 8/2000 | Bahmanyar et al. |
| 6,893,432 B2 | 5/2005 | Intintoli et al. |
| 7,189,226 B2 | 3/2007 | Auld et al. |
| 7,302,142 B2 | 11/2007 | Conde |
| 7,448,995 B2 | 11/2008 | Wiklof |
| 7,566,173 B2 | 7/2009 | Auld et al. |
| 8,398,240 B2 | 3/2013 | Smith |
| 8,488,930 B2 | 7/2013 | Papac |
| 8,498,506 B2 | 7/2013 | Smith |
| 8,561,280 B2 | 10/2013 | Diao et al. |
| 8,571,364 B2 | 10/2013 | Smith |
| 8,764,261 B2 | 7/2014 | Smith |
| 8,903,475 B2 | 12/2014 | Brennan et al. |
| 8,939,964 B2 | 1/2015 | Smith |
| 8,951,244 B2 | 2/2015 | Smith |
| 8,968,347 B2 | 3/2015 | McCollam |
| 9,055,885 B2 | 6/2015 | Horvath |
| 9,107,730 B2 | 8/2015 | Huculak et al. |
| 9,211,214 B2 | 12/2015 | Rubinchik |
| 9,308,128 B2 | 4/2016 | Smith |
| 9,364,982 B2 | 6/2016 | Schaller |
| 9,387,040 B2 | 7/2016 | Smith |
| 9,402,643 B2 | 8/2016 | Auld |
| 9,681,793 B2 | 6/2017 | Artsyukhovich |
| 10,012,800 B2 | 7/2018 | Diao |
| 10,016,302 B2 | 7/2018 | Shazly |
| 10,111,778 B2 | 10/2018 | Smith |
| 10,245,181 B2 | 4/2019 | Diao |
| 10,433,718 B2 | 10/2019 | Liolios |
| 10,441,157 B2 | 10/2019 | Smith |
| 2002/0045811 A1 | 4/2002 | Kittrell |
| 2003/0219202 A1* | 11/2003 | Loeb .................. A61B 18/245 385/33 |
| 2004/0236183 A1 | 11/2004 | Durell |
| 2006/0184162 A1 | 8/2006 | Smith |
| 2008/0027418 A1* | 1/2008 | Berry ..................... A61F 9/008 606/5 |
| 2008/0051770 A1 | 2/2008 | Scheller et al. |
| 2008/0177257 A1 | 7/2008 | Smith et al. |
| 2008/0215041 A1 | 9/2008 | Zemmouri |
| 2008/0243108 A1 | 10/2008 | Murakami |
| 2009/0270850 A1 | 10/2009 | Zhou |
| 2009/0287196 A1 | 11/2009 | Zelickson |
| 2009/0287197 A1 | 11/2009 | Hanley |
| 2010/0027943 A1 | 2/2010 | Armani |
| 2010/0261961 A1 | 10/2010 | Scott |
| 2011/0122366 A1 | 5/2011 | Smith |
| 2011/0144627 A1 | 6/2011 | Smith |
| 2012/0191078 A1 | 7/2012 | Yadlowsky |
| 2013/0150839 A1 | 6/2013 | Smith |
| 2014/0180264 A1 | 6/2014 | Diao et al. |
| 2014/0194862 A1 | 7/2014 | Smith et al. |
| 2014/0200566 A1 | 7/2014 | Smith |
| 2014/0250668 A1 | 9/2014 | Smith |
| 2015/0351629 A1 | 12/2015 | Wheatley |
| 2015/0366432 A1 | 12/2015 | Artsyukhovich |
| 2016/0022119 A1* | 1/2016 | Shah ..................... G02B 23/26 600/182 |
| 2016/0178844 A1 | 6/2016 | Griffin |
| 2016/0302868 A1* | 10/2016 | Nagale .................. A61B 18/24 |
| 2017/0363856 A1* | 12/2017 | Schoeler ............ G02B 23/2476 |
| 2018/0055596 A1 | 3/2018 | Johnson |
| 2018/0243136 A1 | 8/2018 | Diao |
| 2018/0243137 A1 | 8/2018 | Diao |
| 2018/0333304 A1 | 11/2018 | Diao |
| 2018/0344528 A1 | 12/2018 | Farley |
| 2019/0142544 A1 | 5/2019 | Horn |
| 2019/0175273 A1 | 6/2019 | Cook |
| 2019/0175300 A1 | 6/2019 | Horn |
| 2019/0175404 A1 | 6/2019 | Cook |
| 2019/0175405 A1 | 6/2019 | Diao |
| 2019/0175406 A1 | 6/2019 | Cook |
| 2019/0175407 A1 | 6/2019 | Bacher |
| 2019/0175408 A1 | 6/2019 | Diao |
| 2019/0209372 A1 | 7/2019 | Farley |
| 2019/0307527 A1 | 10/2019 | Grueebler |
| 2019/0365569 A1 | 12/2019 | Skovgaard |
| 2020/0107960 A1 | 4/2020 | Bacher et al. |

FOREIGN PATENT DOCUMENTS

| | | |
|---|---|---|
| WO | WO9208427 A2 | 9/1992 |
| WO | WO2001037769 A1 | 5/2001 |
| WO | WO2008024848 A2 | 2/2008 |
| WO | WO2018113887 A2 | 6/2018 |

* cited by examiner

Position a window in an opening of a cannula, at least a portion of the cannula including a shape-memory material in a martensitic phase
502

Transition the shape memory material from the martensitic phase to an austenitic phase to secure the window in position at the opening of the cannula
504

SURGICAL PROBE WITH SHAPE-MEMORY MATERIAL

PRIORITY CLAIM

This application claims the benefit of priority of U.S. Provisional Patent Application Ser. No. 62/597,550 titled "SURGICAL PROBE WITH SHAPE-MEMORY MATERIAL", filed on Dec. 12, 2017, whose inventors are Christopher Cook, Alireza Mirsepassi and Kambiz Parto, which is hereby incorporated by reference in its entirety as though fully and completely set forth herein.

BACKGROUND

Generally, surgical instruments are tools or devices designed to perform specific actions involved in carrying out desired effects during surgery or operations. Ophthalmic surgery typically includes performing an operation on an eye or its adnexa. Often ophthalmic surgeries utilize a probe. Further, these surgeries may include operations on the anterior portions of the eye as well as operations on the posterior portions of the eye. In various embodiments, ophthalmic surgery may be performed on a patient for therapeutic purposes.

DETAILED DESCRIPTION

Various embodiments are generally directed to a surgical probe with shape-memory material, such as a probe with a set of light sources, for instance. Some embodiments are particularly directed to a cannula with a shape-memory material that is used to secure a window. In one or more embodiments, for example, an apparatus for surgical use may include a cannula with a shape-memory material in an austenitic phase. In one or more such embodiments, the cannula may include a tubular structure with first and second ends. In some embodiments, an optical fiber array may extend from the first end toward the second end. In various embodiments, a window may be disposed at the second end of the cannula. In one or more embodiments, a lens may be disposed between the optical fiber array and the window. In some embodiments, the window may be positioned at an opening of the cannula when the shape-memory material is in a martensitic phase. In some embodiments, transitioning the shape-memory material from the martensitic phase to the austenitic phase secures the window in position at the opening of the cannula.

The high power requirements of a probe may present certain challenges. In some embodiments, a probe may include a multi-spot laser that uses high power, such as one to three watts of power. In various embodiments, a lens may become disconnected from a cannula at the temperatures associated with the high-power requirements. For example, adhesives used to attach a lens to a cannula may fail. In some embodiments, the high-power requirements may cause catastrophic failure, such as by causing the cannula and/or the lens to melt. Adding further complexity, fluids, such as blood, may cause light attenuation, which may affect the optical properties of the lens and may increase temperature leading to the above effects.

Various embodiments described herein include a probe that includes a window disposed between a lens and the end of a cannula. In various example embodiments, the window may comprise sapphire or fused silica. In one or more embodiments, the window may extend beyond the end of the cannula. In one or more such embodiments, extending the window beyond the end of the cannula may reduce the reflection of light from the window into the lens. In some embodiments, the window may include an anti-reflective coating. In some embodiments, the window and/or its placement may prevent the lens from exposure to excessive temperatures. In some embodiments, this may lead to a safer and better performing probe. In one or more embodiments, the cannula may comprise a shape-memory material, such as nitinol. In one or more embodiments, the shape-memory material, in an austenitic phase, may couple the cannula to the window. In various such embodiments, the shape-memory material, in a martensitic phase, may result in the cannula having a larger diameter in which the window is not coupled to the cannula. In these and other ways, one or more of the probes described herein may function in a safe and efficient manner to achieve better performing probes, resulting in several technical effects and advantages.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. The intention is to cover all modifications, equivalents, and alternatives within the scope of the claims.

Figure 1:
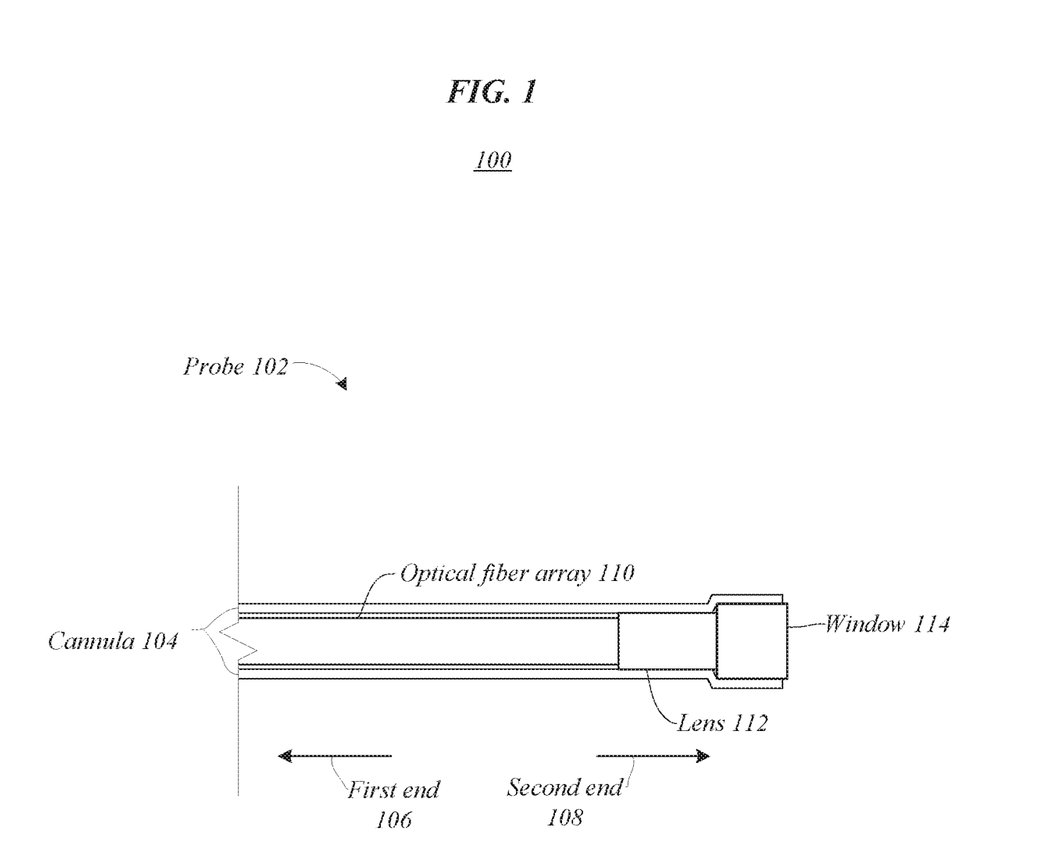
FIG. 1 illustrates an exemplary probe according to one or more embodiments described herein.

FIG. 1 illustrates an embodiment of an operating environment 100 that may be representative of various embodiments. Operating environment 100 may include probe 102. In many embodiments, the probe 102 may include a cannula 104 having a tubular structure with first and second ends 106, 108, an optical fiber array 110, a lens 112, and a window 114. In one or more embodiments described here, the cannula may include a shape-memory material, such as a metal alloy of nickel and titanium, or nitinol. In one or more such embodiments, the shape-memory material may attach the window 114 to the cannula 104 when it is in an austenitic phase. In various embodiments, the window 114 may reduce exposure of the lens 112 to heat, such as when optical fiber array 110 is providing or generating one or more light sources. Embodiments are not limited in this context.

In one or more embodiments, probe 102 may be used in a surgery, such as an ophthalmic surgery. In some embodiments, probe 102 may provide one or more simultaneous light sources, such as laser spots, that may be used to perform specific actions involved in carrying out desired effects during a surgery. In some embodiments, the power per light source may be, for example, between 200 and 600 milliwatts (mW). In various embodiments, optical fiber array 110 may include a set of optical fibers, each of which may provide a light source by passing light through lens 112 and out window 114. In some embodiments, the light sources may be used for photocoagulation and/or illumination. For example, probe 102 may provide four light sources that can be used for photocoagulation in an ophthalmic surgery. In such examples, the combined power of probe 102 may be between 800 and 2400 mW. In one or more embodiments, the combined power of probe 102 may exceed 3 watts.

In some embodiments, the cannula 104 may include a tubular structure with first end 106 and second end 108. In one or more embodiments, the optical fiber array 110 may extend from the first end 106 toward the second end 108. In various embodiments, window 114 may be disposed at the second end 108 of the cannula 104. In various such embodiments, the shape-memory material in cannula 104 may constrict around window 114 to secure a position of the window 114. For instance, the shape-memory material of cannula 104 may create a frictional or mechanical lock with window 114 to secure the position of the window 114. In some embodiments, the lens 112 may be disposed between the optical fiber array 110 and the window 114. In various embodiments, window 114 may not be included. In some such embodiments, the shape-memory material in cannula 104 may constrict around lens 112 instead of window 114 to secure a position of the lens 112. In one or more embodiments, the lens 112 may include a gradient index (GRIN) lens. In various embodiments, window 114 may reduce the amount of heat that the lens 112 is exposed to. In various such embodiments, a position of the lens 112 within cannula 104 may be fixed using adhesive. In some embodiments, lens 112 may be attached to the window 114 with adhesive. In one or more embodiments, an index of refraction of the lens 112 may be correlated with a diameter of the lens 112.

In various embodiments, window 114 may comprise an optically clear material. In various such embodiments, window 114 may be able to withstand temperatures associated with the high-power demand of probe 102. In one or more embodiments, window 114 may be robust enough to withstand stresses associated with coupling with the shape-memory material of the cannula 104. In some embodiments, window 114 may comprise sapphire or fused silica. In some such embodiments, sapphire and fused silica may be examples of optically clear materials that are robust enough to survive the temperatures and stresses associated with operation of the probe 102.

Figure 2:
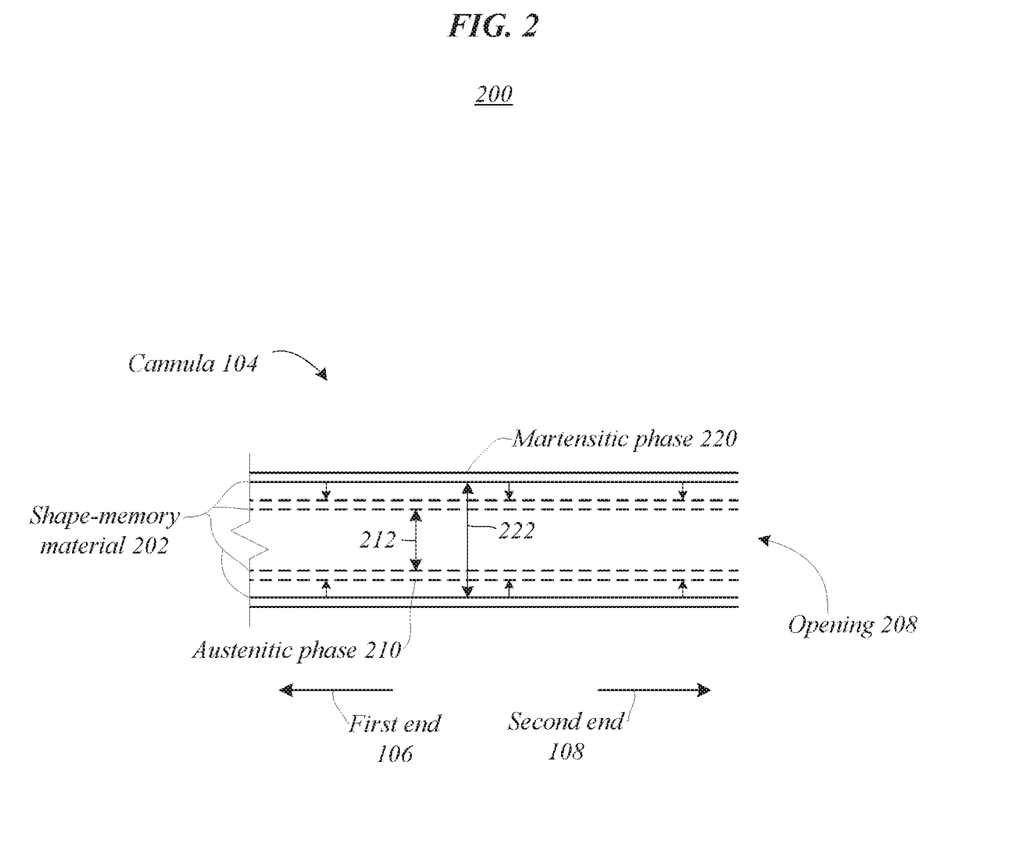
FIG. 2 illustrates an exemplary cannula with shape-memory material according to one or more embodiments described herein.

FIG. 2 illustrates an embodiment of an operating environment 200 that may be representative of various embodiments. Operating environment 200 may include cannula 104 with shape-memory material 202. In various embodiments described herein, shape-memory material 202 may be able to transition between an austenitic phase 210 and a martensitic phase 220. In one or more embodiments, when shape-memory material 202 is in the austenitic phase 210, the tubular structure of cannula 104 may have a first diameter 212. In one or more such embodiments, when shape-memory material 202 is in the martensitic phase 220, the tubular structure of cannula 104 may be expanded to second diameter 222. In the illustrated embodiment, the austenitic diameter 212 may be smaller than the martensitic diameter. Embodiments are not limited in this context.

In some embodiments, shape-memory material 202 may transition to the martensitic phase 220 when the shape-memory material 202 is sufficiently cooled. For example, shape-memory material 202 may transition to the martensitic phase 220 when it is cooled below freezing or at other low temperatures suitable for the material used. In one or more embodiments, shape-memory material 202 may transition to the austenitic phase 210 when it is heated above freezing or to room temperature or to other temperatures suitable for the material used. In various embodiments, when shape-memory material 202 transitions from the austenitic phase 210 to the martensitic phase 220, it may become malleable such that it can be expanded. For example, the first diameter 212 may be expanded to second diameter 222. In some embodiments, when shape-memory material 202 transitions from the martensitic phase 220 to the austenitic phase 210, it may contract. In some such embodiments, this contraction may be used to secure a position of one or more of optical fiber array 110, lens 112, and window 114. In one or more embodiments, shape-memory material 202 may form a seal with one or more of optical fiber array 110, lens 112, and window 114. For example, when the shape-memory material 202 of the cannula 104 is transitioned from the martensitic phase 220 to the austenitic phase 210 it may transition from a first diameter (the martensitic diameter 222) to a second diameter (the austenitic diameter 212) that is smaller than the first diameter. When the shape-memory material 202 transitions in this way, the shape-memory material 202 may compress around window 114 to seal opening 208, thereby securing the window 114 within the cannula 104. In one or more embodiments, shape-memory material 202 may comprise nitinol.

In various embodiments, disposing at least a portion an object, such as window 114, into opening 208 of cannula 104, then transitioning the shape-memory material 202 to the austenitic phase 210 can secure a position of the object with respect to cannula 104 with a mechanical or frictional lock. In one or more embodiments, objects disposed within cannula 104 may prevent a portion of the shape-memory material 202 from reaching the final austenitic diameter 212. In one or more such embodiments, the shape-memory material 202 may compress around the object. For instance, the object may comprise window 114. In such instances, a frictional or mechanical lock may be created between cannula 104 and window 114 by compression of the shape-memory material 202 around window 114. In some embodiments, shape-memory material 202 may comprise one or more portions of cannula 104. For instance, cannula 104 may be entirely constructed of shape-memory material 202. In another instance, only a portion of cannula 104 proximate the second end 108 may include shape-memory material 202.

Figure 3A:
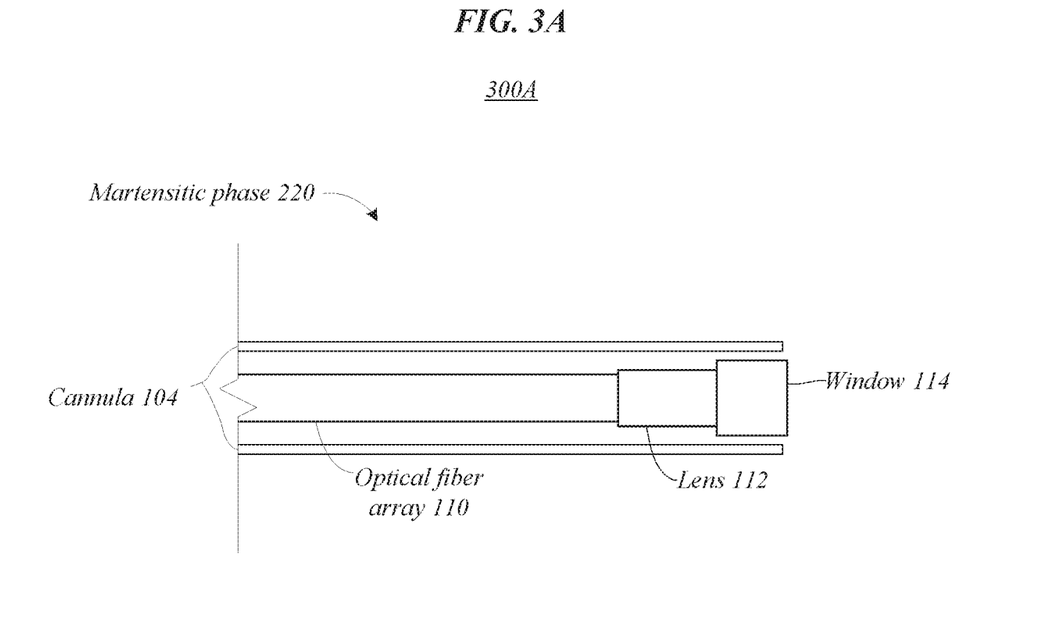
FIGS. 3A and 3B illustrate exemplary shape-memory phases according to one or more embodiments described herein.
Figure 3B:
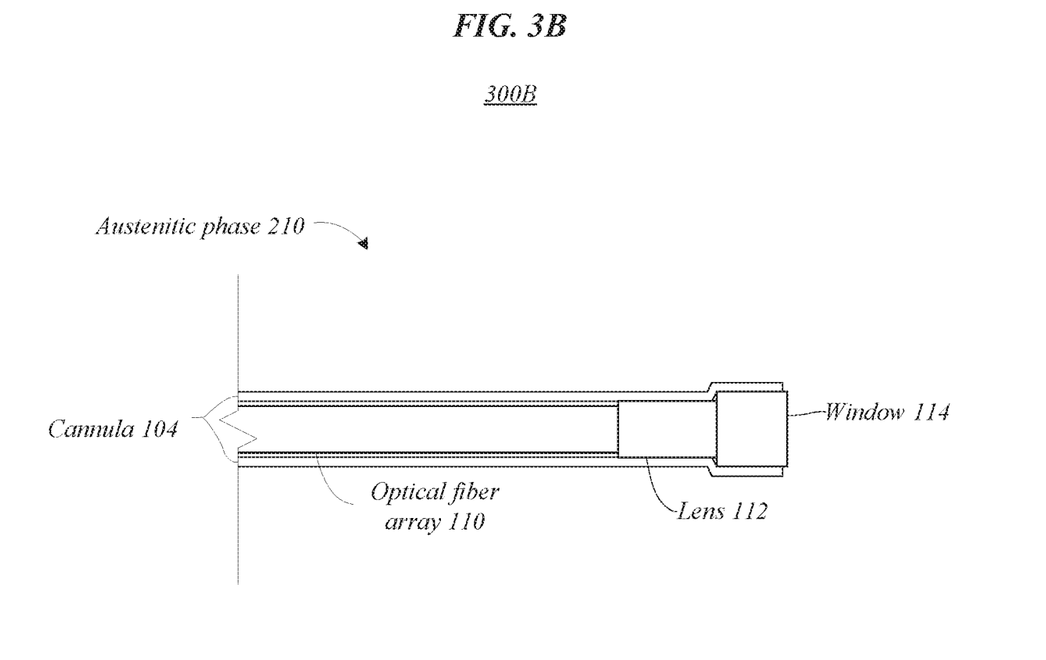

FIGS. 3A and 3B illustrate embodiments of operating environments 300A and 300B that may be representative of various embodiments of cannula 104 with portions of optical fiber array 106, lens 108, and window 114 disposed therein. Operating environment 300A may include cannula 104 in the martensitic phase 220. Operating environment 300B may include cannula 104 in the austenitic phase 210. In one or more embodiments described herein, the portions of optical fiber array 110, lens 112, and window 114 may be positioned within the tubular structure of cannula 104 when the cannula 104 is in the martensitic phase 220. In one or more such embodiments, the positions of one or more of the portions of the optical fiber array 110, lens 112, and window 114 may be secured within the tubular structure of the cannula 104 when the cannula 104 is transitioned from the martensitic phase 220 to the austenitic phase 210. Embodiments are not limited in this context.

In some embodiments, a portion of window 114 may extend past the second end 108 and/or out of the opening 208 of cannula 104. For example, window 114 may extend between 50 and 300 microns past the second end 108 and/or out of the opening 208 of cannula 104. In embodiments without window 114, lens 112 may instead extend past the second end 108 and/or out of the opening 208 of cannula. In various embodiments, extending a portion of window 114 may reduce an amount of light being reflected back into the lens 112 by window 114. In one or more embodiments, window 114 may include an anti-reflective coating to reduce the amount of light being reflected back into the lens 112 by window 114. In some embodiments, preventing light from being reflected back into lens 112 by window 114 may reduce the accumulation of heat within cannula 104.

As previously mentioned, when cannula 104 transitions from the martensitic phase 220 to the austenitic phase 210 with an object disposed therein, one or more portions of cannula 104 may not reach the austenitic diameter 212. Accordingly, as illustrated in operating environment 300B, window 114 has prevented a portion of cannula 104 from reaching the austenitic diameter 212. In such embodiments, by preventing cannula 104 from reaching the austenitic diameter 212, cannula 104 forms a friction or mechanical lock with window 114.

Figure 4A:
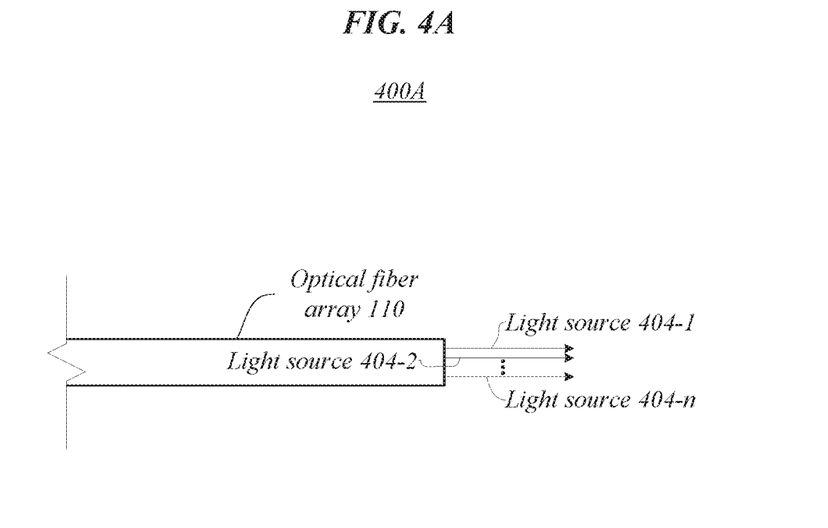
FIGS. 4A and 4B illustrate exemplary light sources according to one or more embodiments described herein.
Figure 4B:
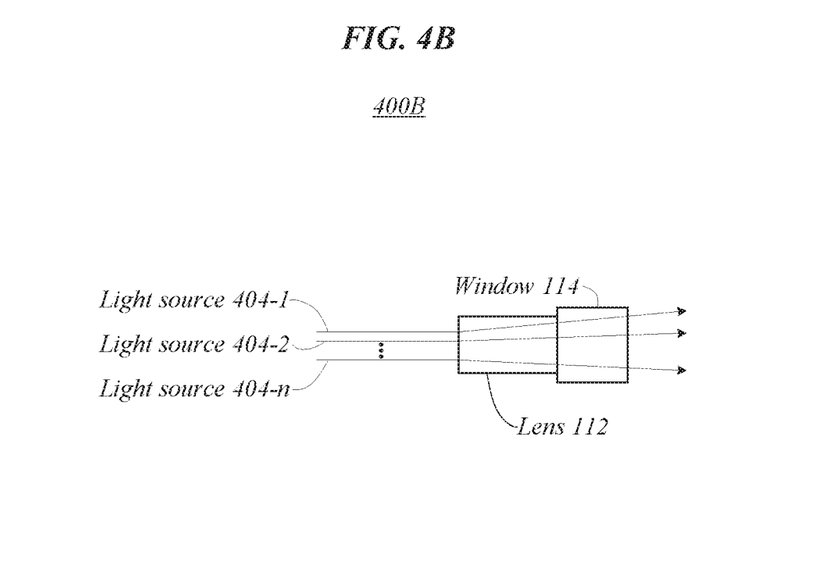

FIGS. 4A and 4B illustrate embodiments of operating environments 400A and 400B that may be representative of various embodiments of light sources 404. In operating environment 400A, optical fiber array 110 may generate one or more light sources 404-1, 404-2, 404-$n$. In one or more embodiments, each light source 404 may correspond to an independent waveguide in optical fiber array 110. In operating environment 400B, each of the one or more light sources 404-1, 404-2, 404-$n$ may pass through lens 112 and out of window 114. In some embodiments, optical fiber array 110 may be in contact with lens 112. In various embodiments, lens 112 may be in contact with window 114. Embodiments are not limited in this context.

In various embodiments, optical fiber array 110 may include one or more waveguides to direct light into lens 112. For instance, optical fiber array 110 may include one or more of fiber optics, a single fiber, a multi-core fiber, and fiber bundles. In one or more embodiments, the light sources 404 may be used in an ophthalmic surgery for one or more of photocoagulation and illumination.

Figure 5:
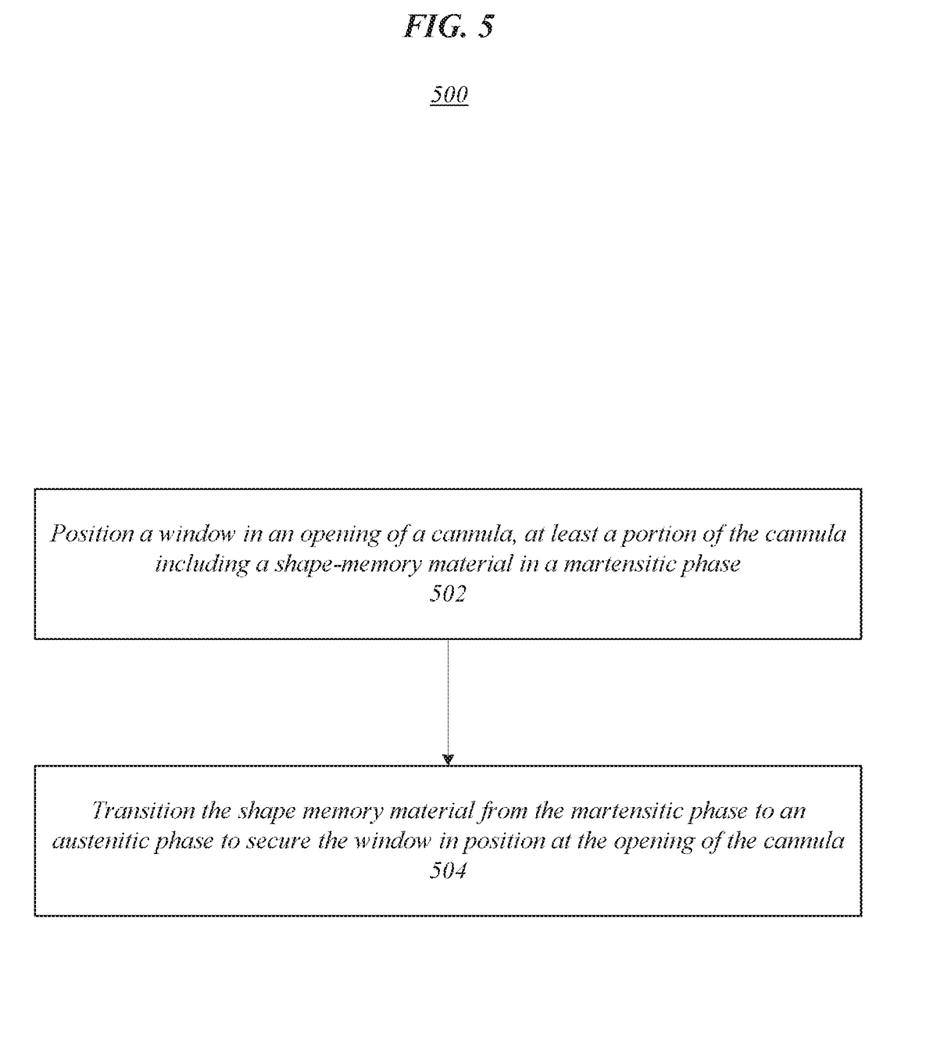
FIG. 5 illustrates an exemplary flow diagram of a method according to one or more embodiments described herein.

FIG. 5 illustrates an embodiment of a flow or method 500, which may be representative of operations that may be executed in various embodiments in conjunctions with securing window 114 to cannula 104 with shape-memory material 202. The flow or method 500 may be representative of some or all of the operations that may be performed to create one or more probes 102 described herein. The embodiments are not limited in this context.

In the illustrated embodiment shown in FIG. 5, the flow or method 500 may begin at 502. At 502 "position a window in an opening of a cannula, at least a portion of the cannula including a shape-memory material in a martensitic phase" a window may be positioned in an opening of a cannula comprising a shape-memory material in a martensitic phase. For instance, window 114 may be positioned in opening 208 of cannula 104 with shape-memory material 202 in martensitic phase 220. In some embodiments, window 114 may be positioned in opening 208 of cannula 104 such that a portion of the window 114 extends out of the opening 208. In some embodiments, the window 114 may extend out of the opening 208 between 200 and 600 microns. In one or more embodiments, the shape-memory material 202 may comprise nitinol.

Proceeding to 504 "transition the shape memory material from the martensitic phase to an austenitic phase to secure the window in position at the opening of the cannula" the shape memory material may be transitioned from the martensitic phase to an austenitic phase to secure the window in position at the opening of the cannula. For example, cannula 104 may be transitioned from the martensitic phase 220 in operating environment 300A to the austenitic phase 210 in operating environment 300B. In various embodiments, transitioning cannula 104 from the martensitic phase 220 to the austenitic phase 210 may secure the window 114 in position at opening 208. In some embodiments, transitioning cannula 104 from the martensitic phase 220 to the austenitic phase 210 may create a seal between cannula 104 and window 114. In some embodiments, the seal between cannula 104 and window 114 may prevent contaminates, such as bodily fluids, from reaching lens 112 during a surgical procedure.

The following examples pertain to further embodiments, from which numerous permutations and configurations will be apparent.

Example 1 is an apparatus for surgical use, comprising: a cannula comprising a shape-memory material in an austenitic phase, the cannula including a tubular structure with first and second ends; an optical fiber array extending from the first end toward the second end; a window disposed at the second end of the cannula; and a lens disposed between the optical fiber array and the window.

Example 2 includes the subject matter of Example 1, wherein the shape-memory material of the cannula is configured so that when the shape-memory material is in a martensitic phase, the cannula has a first diameter at which the window is not secured at the second end of the cannula.

Example 3 includes the subject matter of Example 2, wherein the shape-memory material of the cannula is configured so that when the shape-memory material is in the austenitic phase, the cannula has a second diameter smaller than the first diameter, wherein at the second diameter of the cannula the window is secured at the second end of the cannula.

Example 4 includes the subject matter of Example 1, wherein the window comprises sapphire or fused silica.

Example 5 includes the subject matter of Example 1, wherein a portion of the window extends past the second end of the cannula.

Example 6 includes the subject matter of Example 5, wherein the window extends between 50 and 300 microns past the second end of the cannula.

Example 7 includes the subject matter of Example 1, wherein the shape-memory material comprises a metal alloy of nickel and titanium.

Example 8 includes the subject matter of Example 1, wherein the window comprises an antireflective coating.

Example 9 includes the subject matter of Example 1, wherein the second end of the cannula comprises at least a portion of the shape-memory material.

Example 10 includes the subject matter of Example 1, wherein the shape-memory material in the austenitic phase creates a seal with the window.

Example 11 includes the subject matter of Example 10, wherein the shape-memory material in a martensitic phase is malleable.

Example 12 includes the subject matter of Example 10, wherein the shape-memory material in the austenitic phase constricts around a portion of the window.

Example 13 includes the subject matter of Example 1, wherein the shape-memory material in the austenitic phase secures a position of the lens.

Example 14 includes the subject matter of Example 1, wherein the shape-memory material in a martensitic phase enables the window to be removed.

Example 15 includes the subject matter of Example 1, wherein a position of the lens within the cannula is fixed with adhesive.

Example 16 includes the subject matter of Example 1, wherein the lens is attached to the window with an adhesive.

Example 17 includes the subject matter of Example 1, wherein the lens comprises a gradient index lens.

Example 18 includes the subject matter of Example 17, wherein an index of refraction of the lens correlates with a radius of the lens.

Example 19 includes the subject matter of Example 1, wherein the optical fiber array comprises a multi-core fiber.

Example 20 includes the subject matter of Example 1, wherein the optical fiber array comprises 4 fibers or a 4-core fiber.

Example 21 includes the subject matter of Example 1, wherein each fiber in the optical fiber array generates a light source.

Example 22 includes the subject matter of Example 21, wherein each of the light source utilizes 200 to 600 milliwatts (mW) of power.

Example 23 includes the subject matter of Example 1, wherein the optical fiber array generates a set of light sources.

Example 24 includes the subject matter of Example 23, wherein the set of light sources utilizes over one watt of power.

Example 25 is a method of making an apparatus for surgical use, comprising: positioning a window at an opening of a cannula, wherein at least a portion of the cannula includes a shape-memory material in a martensitic phase, the cannula having a first diameter when the shape-memory material is in the martensitic phase; and transitioning the shape-memory material from the martensitic phase to an austenitic phase, wherein the cannula has a second diameter smaller than the first diameter when the shape-memory material is in the austenitic phase, and wherein when the cannula has the second diameter the cannula secures the window in position at the opening of the cannula.

Example 26 includes the subject matter of Example 25, wherein transitioning the shape-memory material from the martensitic phase to the austenitic phase secures a lens in position within the opening of the cannula.

Example 27 includes the subject matter of Example 26, wherein the lens comprises a gradient index lens.

Example 28 includes the subject matter of Example 27, wherein an index of refraction of the lens correlates with a radius of the lens.

Example 29 includes the subject matter of Example 25, wherein the window comprises sapphire or fused silica.

Example 30 includes the subject matter of Example 25, wherein positioning the window at the opening of the cannula comprises positioning the window at the opening of the cannula such that a portion of the window extends out of the opening of the cannula.

Example 31 includes the subject matter of Example 30, wherein the window extends between 50 and 300 microns out of the opening of the cannula.

Example 32 includes the subject matter of Example 25, comprising attaching a lens to the window with an adhesive.

Example 33 includes the subject matter of Example 25, wherein the shape-memory material comprises a metal alloy of nickel and titanium.

Example 34 includes the subject matter of Example 25, wherein the window comprises an antireflective coating.

Example 35 includes the subject matter of Example 25, wherein an optical fiber array is located inside the cannula.

Example 36 includes the subject matter of Example 35, wherein the optical fiber array comprises a multi-core fiber.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

The invention claimed is:

1. An apparatus for surgical use, comprising:
    a cannula comprising a shape-memory material in an austenitic phase, the cannula including a tubular structure with first and second ends, wherein the shape-memory material comprises a metal alloy of nickel and titanium;
    a multi-core fiber extending from the first end toward the second end;
    a sapphire window disposed at the second end of the cannula, wherein a portion of the window extends past the second end of the cannula; and
    a gradient index lens disposed between the multi-core fiber and the sapphire window;
    wherein the shape-memory material of the cannula is configured so that when the shape-memory material is in a martensitic phase, the cannula has a first diameter at which the sapphire window is not secured at the second end of the cannula;
    wherein the shape-memory material of the cannula is configured so that when the shape-memory material is in the austenitic phase, the cannula has a second diameter smaller than the first diameter, wherein the cannula is in contact with and seals around the sapphire window when the cannula has the second diameter to secure the sapphire window to the second end of the cannula;
    wherein the sapphire window extends out of the opening of the cannula between 50 and 300 microns to inhibit light from being reflected back into the gradient index lens by the sapphire window.

2. The apparatus of claim 1, wherein the sapphire window comprises an antireflective coating.

3. A method of making an apparatus for surgical use, comprising:
    positioning a sapphire window at an opening of a cannula, wherein at least a portion of the cannula includes a shape-memory material in a martensitic phase, the cannula having a first diameter when the shape-memory material is in the martensitic phase, wherein the shape-memory material comprises a metal alloy of nickel and titanium and wherein positioning the sapphire window at the opening of the cannula comprises positioning the sapphire window at the opening of the cannula such that a portion of the sapphire window extends out of the opening of the cannula; and
    positioning a multi-core fiber inside the cannula configured to direct light toward the sapphire window;
    transitioning the shape-memory material from the martensitic phase to an austenitic phase, wherein the cannula has a second diameter, at the opening of the cannula, smaller than the first diameter when the shape-memory material is in the austenitic phase, and wherein when the cannula has the second diameter the cannula secures the sapphire window in position at the opening of the cannula;

wherein transitioning the shape-memory material from the martensitic phase to the austenitic phase also secures a gradient index lens in position within the cannula, and wherein the sapphire window extends out of the opening of the cannula far enough between 50 and 300 microns to inhibit light from being reflected back into the gradient index lens by the sapphire window;

wherein the cannula is in contact with and seals around the sapphire window when the cannula has the second diameter to secure the sapphire window to the opening of the cannula.

4. The method of claim 3, wherein the sapphire window comprises an antireflective coating.

5. The apparatus of claim 1, wherein the cannula is in contact with and constricts around the sapphire window when the cannula is at the second diameter to secure the sapphire window to the second end of the cannula.

6. The apparatus of claim 5, wherein the shape-memory material of the cannula creates a frictional or mechanical lock with the sapphire window when the cannula is at the second diameter.

7. The apparatus of claim 1, wherein the gradient index lens is secured in position within the cannula between the sapphire window and the multi-core fiber when the shape-memory material is in the austenitic phase.

8. The method of claim 3, wherein the shape-memory material of the cannula creates a frictional or mechanical lock with the sapphire window when the cannula has the second diameter.

9. The apparatus of claim 1, wherein the sapphire window is a distal most point of the apparatus such that as light from the gradient index lens travels through and exits the sapphire window, the light directly exits the apparatus.

10. The method of claim 3, wherein the sapphire window is positioned at a distal most point of the apparatus such that as light from the gradient index lens travels through and exits the sapphire window, the light directly exits the apparatus.

* * * * *